(12) United States Patent
Frost et al.

(10) Patent No.: US 7,048,887 B2
(45) Date of Patent: *May 23, 2006

(54) PROCESS AND APPARATUS FOR STERILIZING OBJECTS

(75) Inventors: Robert Frost, Landshut (DE); Peter Awakowicz, Munich (DE)

(73) Assignee: Ruediger Haaga GmbH, Altoberndorf (DE)

( * ) Notice: Subject to any disclaimer, the term of this patent is extended or adjusted under 35 U.S.C. 154(b) by 572 days.

This patent is subject to a terminal disclaimer.

(21) Appl. No.: 09/941,925

(22) Filed: Aug. 30, 2001

(65) Prior Publication Data
US 2002/0054826 A1    May 9, 2002

(30) Foreign Application Priority Data
Aug. 30, 2000    (DE) .............................. 100 42 416

(51) Int. Cl.
*A61L 2/00*    (2006.01)

(52) U.S. Cl. .................... 422/26; 422/1; 422/3; 422/27; 422/28; 422/33; 422/292; 422/293; 422/295; 422/298

(58) Field of Classification Search ................ 422/1, 422/3, 26, 28, 27, 33, 292, 293, 295, 298, 422/297
See application file for complete search history.

(56) References Cited

U.S. PATENT DOCUMENTS

| 4,797,255 A | | 1/1989 | Hatanaka et al. |
| 4,952,370 A | * | 8/1990 | Cummings et al. ........... 422/28 |
| 5,173,259 A | * | 12/1992 | Bordini ........................ 422/28 |
| 5,525,295 A | * | 6/1996 | Pflug et al. ................... 422/27 |

FOREIGN PATENT DOCUMENTS

EP    0243003 B1    3/1994

* cited by examiner

*Primary Examiner*—Krisanne Jastrzab
(74) *Attorney, Agent, or Firm*—Crowell & Moring LLP

(57) ABSTRACT

In a process for sterilizing objects, the surfaces of the objects are dampened by condensating a steam compound of water and hydrogen peroxide. The steam compound reaches hereby the objects to be sterilized without any additional transport gas flow. Subsequent drying occurs by means of evacuation at a pressure below the boiling points of water and hydrogen peroxide.

6 Claims, 1 Drawing Sheet

PROCESS AND APPARATUS FOR STERILIZING OBJECTS

BACKGROUND AND SUMMARY OF THE INVENTION

This application claims the priority of German patent application 100 42 416.3, filed in Germany, Aug. 30, 2000, the disclosure of which is expressly incorporated by reference herein.

The present invention relates to a process for sterilizing objects on their surfaces, which are dampened by means of condensing a steam compound of water and hydrogen peroxide, whereby the condensation fluid is subsequently removed from the surfaces by means of drying.

In sterilization using hydrogen peroxide, which is always present in the form of a watery solution, a purely chemical sterilizing process takes place effected by the "activated" hydrogen peroxide. The term "to activate" used here is undefined, yet a chemical and/or physical reaction takes place as a result of the addition of heat to the hydrogen peroxide, which then effects the sterilization. In a cool state, namely at room temperature or slightly above, hydrogen peroxide has practically no technically applicable sterilizing effect.

In practice, various procedures are known for "activating" hydrogen peroxide for the purpose of sterilizing.

In a known process, European published patent 0 243 003 (corresponding U.S. Pat. No. 4,797,255), a solution comprising water and hydrogen peroxide vaporizes and is fed by a hot transporting air flow to the cooler surfaces, where atmospheric pressure prevails, which cooler surfaces are to be dampened by the condensation of the steam compound. The subsequent drying process takes place by a separate hot air flow.

In the known process, the "activating" of the hydrogen peroxide takes place exactly then when it is required for sterilization, that is, during condensation. Due to the transporting air flow, the concentration of the hydrogen peroxide is, unfortunately, reduced. In addition to this, it cannot be guaranteed that the fed transporting air flow actually reaches all the surfaces to be sterilized. Finally, the subsequent drying process is time-consuming due to the renewed feeding of hot air.

It is an object of the present invention to improve the sterilization effect and to reduce the duration of the sterilizing process.

This object has been achieved in accordance with the present invention in that dampening by means of condensation of the steam compound is carried out without an additional transport gas flow, and in that the drying process is carried out by means of evacuation at a pressure below the boiling points for water and hydrogen peroxide.

In the process according to the present invention, the "activating" of the hydrogen peroxide takes place as in prior art exactly then, when it is required for sterilization, namely during condensation. But because the steam compound reaches the objects to be sterilized without additional transport gas flow, the concentration of hydrogen peroxide during sterilization is significantly higher. The removal of hydrogen peroxide traces is not carried out by subsequent heating, but rather by simple evacuation at a pressure below the boiling points of water and hydrogen peroxide, which process is executed in seconds and reliably removes all traces of hydrogen peroxide.

The steam compound of water and hydrogen peroxide necessary for sterilization is generated in an evaporator or gasifier, the design of which is irrelevant for the purpose of the present invention, as long as it is capable of generating a high enough concentration of hydrogen peroxide steam in a steam compound. The actual "activating" of the hydrogen peroxide in the steam compound takes place during condensation on the surfaces to be sterilized. The steam compound is caused to dampen the surfaces with as thin and homogenous a film of fluid as possible. A microscopically thin condensation layer, barely visible to the naked eye, is sufficient for the purpose of the present invention in order to achieve a sterilizing effect in the shortest time possible. Because of the thinness of the layer, the undesirable formation of ice during subsequent drying by means of evacuation does not arise.

The steam compound to be fed into the treatment chamber for sterilizing is determined by the total condensation surface area available. The volume of the sterilization chamber itself is not an important factor, as it is only on the surfaces that condensation occurs.

The applicant supposes that, in connection with the "activating" of the hydrogen peroxide, the following circumstances could be of significance.

The boiling point of hydrogen peroxide is higher than that of water. This means that, when cooling, the hydrogen peroxide condensates first, followed then by the water. It is therefore supposed that a condensation layer of mostly pure fluid hydrogen peroxide arises, on which lies a layer of water condensation. This results particularly on the surfaces to be sterilized, exactly at the right moment, seemingly to an additional increase in the concentration of the hydrogen peroxide in the steam compound.

Tests have shown that a steam compound having at least 25% hydrogen peroxide should be generated and subsequently brought into contact with the surfaces to be sterilized. It has been shown that the required time for sterilizing decreases with the increase in concentration of the hydrogen peroxide in the condensation fluid. The watery solution used for evaporating or gasifying should preferably contain 35% to 60% hydrogen peroxide. It is, however, to ensure a reliable process, helpful to introduce a predetermined amount of hydrogen peroxide solution into the evaporator or gasifier, whereby this amount is completely evaporated, so that the hydrogen peroxide concentration in the steam compound is equal to the concentration of the introduced watery solution.

The process according to the present invention can be carried out in a large variety of ways, depending on the application or on the objects to be sterilized.

In one process according to the present invention, for example, the steam compound is generated in an evaporator, which serves at the same time as a sterilization chamber, through which the dampened objects are guided. This process is in particular for the sterilization of sheet material, from which, for example, plastic cups are subsequently punched. During the passage of the sheet material through the evaporator, the condensation fluid is deposited on the colder sheet material and causes a sterilizing effect. The condensation fluid can then be removed in a downstream drying chamber by means of vacuum pumping. In this process, the pressure of the evaporator is the same as that of the sterilization chamber, which is a part of the evaporator. Thus it is ensured that the steam compound reaches all surfaces to be sterilized.

In another process according to the present invention it is provided that the steam compound is generated in an evaporator and subsequently, for the purpose of dampening the objects by means of condensation, is guided into a separate sterilization chamber, whose pressure is significantly lower than the steam pressure of the steam compound. This latter named process is thus a low pressure or vacuum process, whereby it is guaranteed that the steam compound reaches all the surfaces to be sterilized.

The pressure area to be considered is determined by the following: the temperature, at which hydrogen peroxide begins to thermally dissolve, is 140° C. This temperature should not therefore be overly exceeded during evaporation. Because of the lower boiling point of water, the steam pressure of more highly concentrated solutions at the same temperature is significantly lower than the steam pressure of water. In the case of the preferred 50% water, 50% hydrogen peroxide solution , the steam pressure measures at, for example, 120° C., approximately 1100 mb. In order that the steam compound of hydrogen peroxide steam and water steam can flow without being diluted by the residual air in the sterilization chamber, the chamber pressure must be significantly lower than the above mentioned steam pressure, in particular when the volume of the sterilization chamber is significantly larger than the volume of the steam compound available in the evaporator. In order for condensation to take place in the sterilization chamber, the chamber pressure must be able to increase significantly as a result of the in-flow of the steam compound. The chamber pressure before the in-flow of the steam compound should be in the range of between 5 and 0.1 mb, for example approximately 1 mb, when the chamber volume is, for example, forty times that of the evaporator volume. If the ratio between chamber volume and evaporator volume is smaller, the chamber pressure can be accordingly higher before the in-flow of the steam compound.

It should be mentioned here that, as a result of the higher temperature together with a very high concentration of the steam compound flowing out of the evaporator, a side effect is that a heated conduit to the sterilization chamber is at the same time sterilized, even without condensation. This is of great importance for fully aseptic applications.

The feeding of the steam compound into the sterilization chamber without additional transport gas flow can take place in two ways, either by means of adiabatic expansion or by means of so-called continuous oversaturation. The transition from adiabatic expansion to continuous oversaturation is to a large extent simple, when adiabatic expansion occurs periodically and the intervals between two expansions are used to return to zero.

In the case of adiabatic expansion, a predetermined amount of the steam compound flows abruptly from the evaporator or gasifier into the sterilization chamber. Due to the speed of the action, the over-all energy contained in the steam compound cannot alter, it remains constant, so that the state alteration is adiabatic. However, during the adiabatic expansion, the volume taken up by the steam compound increases greatly, as the steam compound must now, in addition to the evaporator volume, also fill out the volume of the sterilization chamber. As a result the temperature is drastically reduced and thus falls very far below the dew point, whereby an extremely oversaturated steam compound arises, so that almost the entire mass contained in the steam compound condensates in the shortest possible time on all the surfaces exposed thereto.

In order to achieve the abrupt expansion, the chamber pressure must be much lower than the pressure in the evaporator. For example, the expansion of a steam compound from 90° C. to double the volume results in a temperature of approximately 10° C., the expansion to ten times the volume results in a temperature of −110° C. The advantage of adiabatic expansion lies above all in the extremely short time required for the generation of a condensation layer. It is therefore preferred in such applications where a particularly short sterilization time is desirable, for example in the case of sterilization of PET bottles.

In the case of another variation, wherein the steam compound flows out of the evaporator into the sterilization chamber due to continuous oversaturation, the steam compound also reaches the sterilization chamber from the evaporator due to the applied pressure drop, whereby, however, the process takes longer. Over a certain time span, a watery solution is continuously evaporated, whereby overpressure in the evaporator is maintained and thus a steam compound can be continuously fed into the sterilization chamber. As the temperature, and thus the pressure, is higher in the evaporator, the steam compound expands in the sterilization chamber, which in turn leads to a cooling down. In addition hereto, however, the pressure in the sterilization chamber is increased due to the continuous follow-on flow of the steam compound. Cooling and pressure increase result in an oversaturation of the steam compound accumulating in the sterilization chamber, as both processes force the state of the steam compound below the dew point. As long as the steam compound is fed in, condensation occurs on all accessible surfaces.

In the continuous oversaturation method, a very large amount of condensation fluid can be generated and precipitated using a relatively small evaporator volume, whereby, however, the process takes up a correspondingly longer amount of time. The chamber pressure of the sterilization chamber need only lie slightly under the pressure of the evaporator, just the amount required for the necessary amount of steam compound to flow in. In the evaporator, the temperature must thus be always high enough to permit the steam pressure to continuously exceed the chamber pressure. Continuous oversaturation is suitable for those applications in which the duration of the sterilization process is not of foremost importance. This latter method offers an additional advantage in the form of the significantly higher temperature of the steam compound, which is not greatly lowered by abrupt, extreme expansion, as well as the capability to condensate on relatively warm surfaces.

In particular in sterilizing larger and more complicated surfaces, it can be advantageous when the dampening by means of condensation, as well as the drying of the condensation, is repeated at least once. Repeated cycles, consisting of condensating with subsequent pumping out of the condensation layer, give better results in certain circumstances than one single extended condensation process lasting for the same duration. In some cases, repeated condensation, without pumping out the condensation layer in between, can delivery improved results.

Although the repeated cycle of condensation and evacuation in a non-generic sterilization process (German published patent application 198 18 224) is generally known, what is involved in the known process is not a chemical sterilization by means of hydrogen peroxide, but rather a purely thermal sterilization process using water saturated steam at a temperature of at least 120° C.

Other objects, advantages and novel features of the present invention will become apparent from the following detailed description of the invention when considered in conjunction with the accompanying drawings.

DETAILED DESCRIPTION OF THE DRAWINGS

Figure 1:
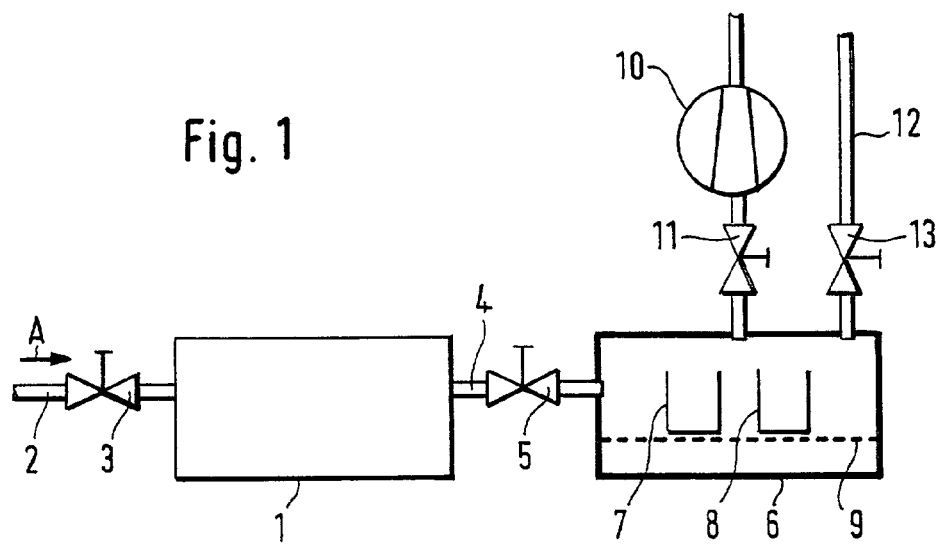
FIG. 1 is a schematic illustration of an installation for carrying out a process in which the steam compound is generated in a evaporator and subsequently fed to a separate sterilization chamber, constructed according to a preferred embodiment of the invention.

In the installation according to FIG. 1, a steam compound of water steam and hydrogen peroxide steam is generated, whereby it is fundamentally unimportant whether, in the case of each type of steam, a wet steam or a superheated steam is involved. The evaporator or the gasifier, which can be of any desired design, is provided with the reference number 1. A watery solution comprising hydrogen peroxide and water in the desired concentration is fed under pressure in direction A via a conduit 2 and a valve 3 to the evaporator 1.

A sterilization chamber 6 is arranged downstream of the evaporator 1, in which sterilization chamber 6 objects 7,8, whose surfaces are to be sterilized, are placed on suitable supports. In the case of containers to be sterilized, these surfaces may even include the sterilization chamber itself.

The sterilization chamber 6 is first evacuated, namely by means of a suitable vacuum pump 10. Subsequently the sterilization chamber 6 is isolated from the vacuum pump 10 by the closing of a valve 11, so that no suction action takes place.

By opening a valve 5, it is ensured that the steam compound present in the evaporator 1 finds its way via the conduit 4 into the sterilization chamber 6, be it by means of adiabatic expansion or continuous oversaturation. The pressure in the evaporator 1 must, as a consequence, be higher than the pressure in the sterilization chamber 6. During expansion, the volume taken up by the steam compound increases, whereby the steam compound cools down greatly below the dew point and condensates on all accessible surfaces of the objects 7 and 8 as well as on the support 9 and the inner surfaces of the sterilization chamber 6, and the pressure in the sterilization chamber 6 increases again. With aid of the vacuum pump 10, the condensation fluid is drawn out within seconds and the sterilization chamber 6 is ventilated with sterile circulation gas via a conduit 12 and a valve 13. The contact time of the condensation fluid with the surfaces to be sterilized can, depending on secondary factors, be less than three seconds.

Figure 2:
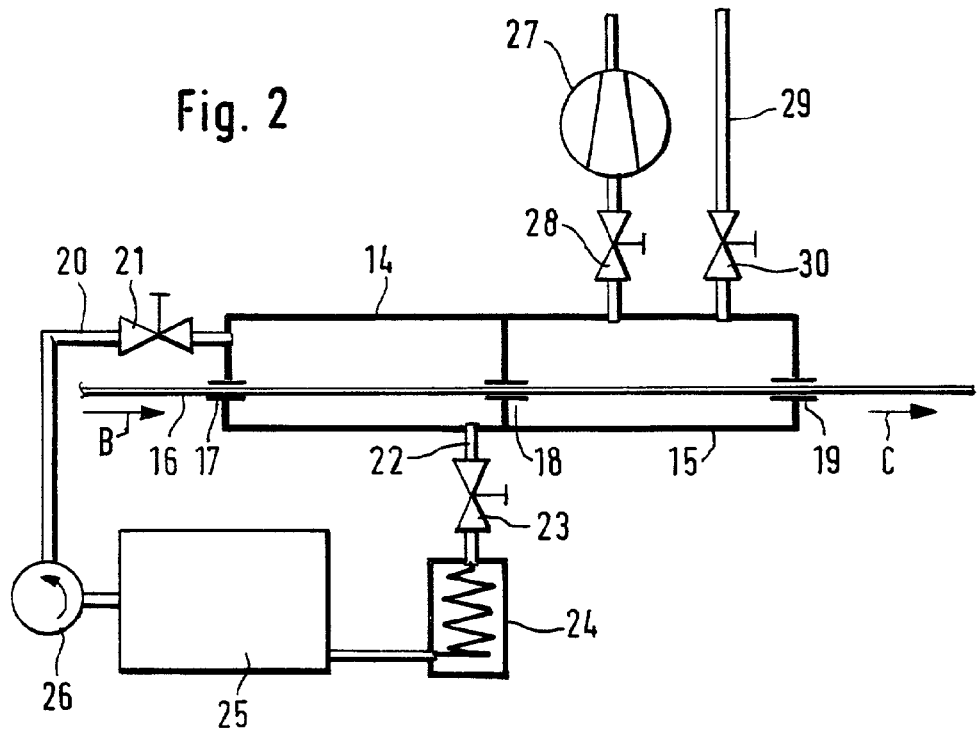
FIG. 2 is a schematic illustration of an installation for carrying out a process, in which the evaporator is at the same time the sterilization chamber, constructed according to another preferred embodiment of the invention.

In the installation according to FIG. 2, sheet material 16 is transported in transport direction B,C through an evaporator 14 and on to a drying chamber 15 arranged downstream thereof. In the case of the sheet material 16, synthetic sheets can be involved here, out of which cups or cans are stamped. In the evaporator 14 as well as in the drying chamber 15, sufficiently tight locks are provided at both entry and exit openings. While the sheet material 16 is passing through the evaporator 14, which is at the same time the sterilization chamber, the condensation fluid can precipitate on the sufficiently cold sheet material 16. In the downstream drying chamber 15, the condensation fluid can be drawn off again by means of a vacuum pump 27 after a valve 28 has been opened. A temperature of between 80° C. and 120° C. in the evaporator 14, which at the same time is the sterilization chamber, does not harm the sheet material 16, as the passing through-time is only two to three seconds. The pressure of the steam compound lies, according to the steam pressure curve, in the range of 300 to 1200 mb. The pressure in the downstream drying chamber 15 should then, depending on the applied hydrogen peroxide concentration and the temperature in the evaporator, lie in the range of between 0.5 and 5 mb.

The drying chamber 15 can be connected to a conduit 29 for sterile circulating gas via a valve 30.

The watery solution of water and hydrogen peroxide having the desired concentration is fed under pressure to the evaporator 14 from a supply tank 25 by means of a pump 26 via a conduit 20 and a valve 21. Precipitated condensation fluid from the evaporator 14 can be precipitated into a condensator 24 via a conduit 22 and a valve 23, where it is again deposited in the supply tank 25.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A process for sterilizing objects on their surfaces, comprising the steps of:
    dampening the object surfaces by condensing a steam compound of water and hydrogen peroxide, and
    removing the condensed fluid from the surfaces by drying,
    wherein the dampening step includes abruptly releasing the steam compound into a sterilizing chamber without additional transport gas flow, so that the steam compound becomes over-saturated and condenses on the surfaces within three seconds, and
    wherein the drying is carried out by evacuation at a pressure below boiling points of water and hydrogen peroxide.

2. A process according to claim 1, wherein the steam compound is generated in an evaporator and subsequently fed into a separate sterilization chamber to dampen the objects, the pressure of the sterilization chamber being lower than the steam pressure of the steam compound.

3. A process according to claim 2, wherein the steam compound flows from the evaporator into the sterilization chamber essentially by means of adiabatic expansion.

4. Apparatus for sterilizing surfaces of objects comprising:
    means for generating a steam compound of water and hydrogen peroxide,
    a sterilization chamber accommodating objects to be sterilized,
    means for dampening surfaces of the objects in the sterilization chamber by abruptly releasing the steam compound into the sterilizing chamber without additional transport gas flow being applied to the steam compound, so that the steam compound becomes over-saturated and condenses on the surfaces within three seconds, and
    means for subsequently removing condensation fluid from the surfaces of the objects by drying carried out by evacuation of the sterilization chamber at a pressure below boiling points of water and hydrogen peroxide.

5. Apparatus according to claim 4, wherein the means for generating a steam compound includes an evaporator chamber separate from the sterilization chamber, and
    wherein means are provided for maintaining the pressure of the sterilization chamber lower than the pressure in the sterilization chamber.

6. Apparatus according to claim 5, wherein the means for dampening the surfaces include means for inducing flow of the steam compound from the evaporator chamber to the sterilization chamber by adiabatic expansion.

* * * * *